(12) United States Patent
Heinonen

(10) Patent No.: US 8,893,718 B2
(45) Date of Patent: Nov. 25, 2014

(54) VALVE AND METHOD TO RELIEVE GASEOUS PRESSURE AND ARRANGEMENT FOR VENTILATING LUNGS

(75) Inventor: Erkki Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 99 days.

(21) Appl. No.: 13/232,335

(22) Filed: Sep. 14, 2011

(65) Prior Publication Data
US 2013/0061852 A1 Mar. 14, 2013

(30) Foreign Application Priority Data
Sep. 15, 2010 (EP) .................... 10176769

(51) Int. Cl.
*A62B 9/02* (2006.01)
*A61M 16/12* (2006.01)
*A61M 16/22* (2006.01)
*A61M 16/20* (2006.01)
*A61M 16/08* (2006.01)
*A61M 16/00* (2006.01)

(52) U.S. Cl.
CPC ....... *A61M 16/12* (2013.01); *A61M 2016/0039* (2013.01); *A61M 16/22* (2013.01); *A61M 16/204* (2013.01); *A61M 16/0891* (2013.01); *A61M 16/209* (2013.01); *A61M 16/0078* (2013.01); *A61M 16/208* (2013.01); *A61M 16/0081* (2013.01); *A61M 2016/0027* (2013.01); *A61M 16/20* (2013.01)
USPC ............ 128/205.24; 128/204.18; 128/204.21; 128/205.13

(58) Field of Classification Search
CPC ............ A61M 16/20; A61M 16/0075; A61M 16/0078; A61M 16/208
USPC ............. 128/204.18, 204.21, 204.23, 205.13, 128/205.24
See application file for complete search history.

(56) References Cited

U.S. PATENT DOCUMENTS 4,883,051 A * 11/1989 Westenskow et al. ... 128/204.21
5,072,729 A * 12/1991 DeVries ................... 128/204.23
(Continued)

FOREIGN PATENT DOCUMENTS

FR 2573658 A1 5/1986

OTHER PUBLICATIONS

Siemens-Elema AB, Electromedical Systems Division, Sevo Ventilator 300/300A—Service Manual, Aug. 1997, 3rd English edition.*

(Continued)

*Primary Examiner* — Justine Yu
*Assistant Examiner* — Timothy Stanis
(74) *Attorney, Agent, or Firm* — GE Global Patent Operation; Marc A. Vivenzio

(57) ABSTRACT

A valve is provided for relieving a gaseous pressure of a branching unit in flow communication with lungs of a subject. The valve comprises an inlet port in flow communication with the branching unit, an outlet port configured to release pressure by discharging a gas flow from the inlet port, and a valve seat in flow communication with the inlet port. The valve further comprises a valve member configured to close a gas discharge between the inlet port and the outlet port when forced against the valve seat, and to facilitate gas discharge between the inlet port and the outlet port when not forced against the valve seat. The valve further comprises a closing spring configured to direct a predetermined closing force to the valve member and an actuator configured to increase and decrease the closing force directed to the valve member.

6 Claims, 2 Drawing Sheets

(56) References Cited

U.S. PATENT DOCUMENTS

| | | | | |
|---|---|---|---|---|
| 5,735,504 | A | * | 4/1998 | Walters ........................... 251/83 |
| 5,881,722 | A | * | 3/1999 | DeVries et al. ........... 128/204.21 |
| 6,148,816 | A | * | 11/2000 | Heinonen et al. ........ 128/205.24 |
| 6,564,798 | B1 | * | 5/2003 | Jalde ........................ 128/205.24 |
| 7,073,502 | B2 | * | 7/2006 | Bromster ................. 128/205.13 |
| 2002/0017301 | A1 | * | 2/2002 | Lundin .................... 128/205.24 |
| 2002/0104538 | A1 | * | 8/2002 | Emtell ..................... 128/205.14 |
| 2004/0144385 | A1 | | 7/2004 | Bromster |
| 2007/0125377 | A1 | * | 6/2007 | Heinonen et al. ........ 128/204.21 |
| 2008/0302363 | A1 | * | 12/2008 | Kroupa .................... 128/204.21 |
| 2009/0314294 | A1 | | 12/2009 | Chalvignac |

OTHER PUBLICATIONS

EP Search Report in connection with EP Patent Application 10176769.7 filed on Sep. 15, 2010, issued on May 19, 2011.

* cited by examiner

VALVE AND METHOD TO RELIEVE GASEOUS PRESSURE AND ARRANGEMENT FOR VENTILATING LUNGS

BACKGROUND OF THE INVENTION

1. Field of the Invention

This disclosure relates generally to a valve to relieve a gaseous pressure in a branching unit having at least three limbs, one of them being for an inspired gas, a second one being for an expired gas and a third one being for both the inspired and expired gases and being in flow communication with lungs of a subject. Also this disclosure relates generally to a method to relieve gaseous pressure in a branching unit providing a breathing gas for a subject inhalation and receiving a breathing gas exhaled. Further this disclosure relates generally to an arrangement for ventilating lungs of the subject.

2. Description of Related Art

During ventilation, a patient's lungs are connected with an artificial ventilation system with breathing circuit. For inspiration during artificial ventilation, the patient's lungs are filled using a ventilator utilizing overpressure. An overpressure pneumatic ventilator adds drive gas to the breathing circuit which forces the breathing gas to the patient's lungs. Alternatively, piston driven ventilators reduce the breathing circuit volume while forcing the gas to flow to the lungs. Delivering additional fresh breathing gas to the lungs using a gas mixer may also increase the breathing circuit and lung pressure and thus participate in the inspiration.

A clinician may also use a manual breathing bag, a flexible container connected pneumatically on the breathing circuit, to pressurize the circuit and patient's lungs for an inspiration. Squeezing the manual bag reduces the breathing circuit volume which increases the circuit pressure and forces the gas to flow to the patient's lungs.

During expiration the overpressure is released by opening a valve allowing the gas to flow out from the pressurized lungs. For the purpose of relieving pressure, the ventilator uses an expiration valve. A control algorithm regulates the flow through the valve in order to reach and maintain required expiration pressure.

During manual ventilation, releasing the bag increases the circuit volume allowing the gas to flow out from the patient's lungs, which results in a reduction of pressure in the lungs. Additional pressure developed in the breathing circuit is released through an adjustable pressure limiting (APL) valve, with which the clinician limits the maximum breathing circuit pressure. Any pressure exceeding the APL limit pressure is relieved through the valve.

An overpressure is the most serious safety risk related to patient ventilation. As a response to a sudden rise in pressure, lung damage may occur before manual relief is possible. Therefore, the ventilation system must be equipped with safety measures configured to automatically prevent the overpressure in normal operation, as well as overpressure resulting from a on a device in, what would otherwise be, single failure operation condition.

In addition to the overpressure, an inability to relieve the breathing circuit pressure may cause a static elevated, sustained, pressure. This compromises gas exchange in the lungs and may cause cardiologic complications.

Situations that may cause an unintentional breathing circuit pressure rise include ventilator or gas mixer failures that limit the gas delivery to the breathing circuit, pressure increases caused by external reasons like patient coughing, or breathing circuit occlusion which prevents or slows down the pressure relief from the breathing circuit.

Particularly in situations involving occlusion of the expiration pathway of the patient, no exhalation gas can be evacuated through the ventilator expiration valve or the APL valve because the gas pathway is blocked. For such situation ventilator safety regulations require a protection against a patient hazard arising in the normal operation or arising from any equipment single failure condition. The pressure at the patient connection port shall be limited to maximum 12.5 kPa. Ventilation systems are equipped with spring-loaded mechanical pressure relief valves for this. A relief limit below the standard requirement would however be desirable specifically for small patients. On the other hand ventilation of obese and some lung-sick patients may require the standard relief limit. Furthermore, during failure situations, these state-of-the-art protection devices only limit the pressure rise whereas total pressure relief would be desirable to stop hazardous sustained pressure. Such total relief can, however, not be continuous, because the ventilation system should still allow a continuation of manual ventilation in the case of ventilator failure or a power supply failure. To allow this, the safety pressure relief valve must remain closed.

BRIEF SUMMARY OF THE INVENTION

The above-mentioned shortcomings, disadvantages and problems are addressed herein which will be understood by reading and understanding the following specification.

In an embodiment, a valve is provided for relieving a gaseous pressure of a branching unit in flow communication with lungs of a subject. The branching unit comprises at least three limbs: one of the at least three limbs is configured for an inspired gas, a second of the at least three limbs is configured for an expired gas, and a third of the at least three limbs is configured for both the inspired and expired gases and is. The valve comprises an inlet port in flow communication with the branching unit, an outlet port configured to release pressure by discharging a gas flow from the inlet port, and a valve seat in flow communication with the inlet port. The valve further comprises a valve member configured to close a gas discharge between the inlet port and the outlet port when forced against the valve seat, and to facilitate gas discharge between the inlet port and the outlet port when not forced against the valve seat. The valve further comprises a closing spring configured to direct a predetermined closing force to the valve member, wherein the valve member is not forced against the valve seat when a force due to the gaseous pressure exerted on the valve member from the inlet port exceeds the predetermined closing force of the closing spring. The valve further comprises an actuator configured to increase and decrease the closing force directed to the valve member.

In another embodiment, a system for ventilating lungs of a subject is provided. The system comprises a gas mixer for supplying a fresh gas for a subject breathing and a breathing circuit for connecting lungs of the subject and the gas mixer. The breathing circuit is configured to provide an inspiration gas comprising the fresh gas for the subject breathing. The breathing circuit comprises a branching unit comprising at least three limbs, wherein one of the at least three limbs is configured for an inspired gas, a second of the at least three limbs is configured for an expired gas, and a third of the at least three limbs is configured for both the inspired and expired gases. The breathing circuit further comprises a valve configured to relieve gaseous pressure in the branching unit. The valve comprises an inlet port in flow communication with the branching unit, an outlet port configured to release pressure by discharging a gas flow from the inlet port, and a valve seat in flow communication with the inlet port. The valve further comprises a valve member configured to close a gas discharge between the inlet port and the outlet port when forced against the valve seat, and to facilitate gas discharge between the inlet port and the outlet port when not forced against the valve seat. The valve further comprises a closing spring configured to direct a predetermined closing force to the valve member, wherein the valve member is not forced against the valve seat when a force due to the gaseous pressure exerted on the valve member from the inlet port exceeds the predetermined closing force of the closing spring. The valve further comprises an actuator configured to increase and decrease the closing force directed to the valve member.

In yet another embodiment a method is provided for relieving gaseous pressure in a branching unit providing a breathing gas for a subject inhalation and receiving an exhaled breathing gas. The branching unit is in flow communication with a valve configured to close a gas discharge with a predetermined closing force when a breathing gas pressure of the branching unit is below a pressure determined by the predetermined closing force and to facilitate the gas discharge when a force due to the breathing gas pressure of the branching unit exceeds the pressure determined by the predetermined closing force. The method comprises determining an allowed branching unit breathing gas pressure limit information, acquiring a signal indicative of a prevailing breathing gas pressure in the branching unit, changing the predetermined closing force if the allowed branching unit breathing gas pressure limit information deviates from the predetermined closing force, comparing the signal indicative of a prevailing breathing gas pressure with the allowed branching unit breathing gas pressure limit information; and if the signal indicative of a prevailing breathing gas pressure deviates from the allowed branching unit breathing gas pressure limit information, changing the closing force to meet the allowed branching unit breathing gas pressure limit information.

Various other features, objects, and advantages of the invention will be made apparent to those skilled in art from the accompanying drawings and detailed description thereof.

BRIEF DESCRIPTION OF THE SEVERAL VIEWS OF THE DRAWINGS

The accompanying drawings, which are incorporated in and constitute a part of the specification, illustrate one or more embodiments and, together with the description, explain these embodiments. In the drawings.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
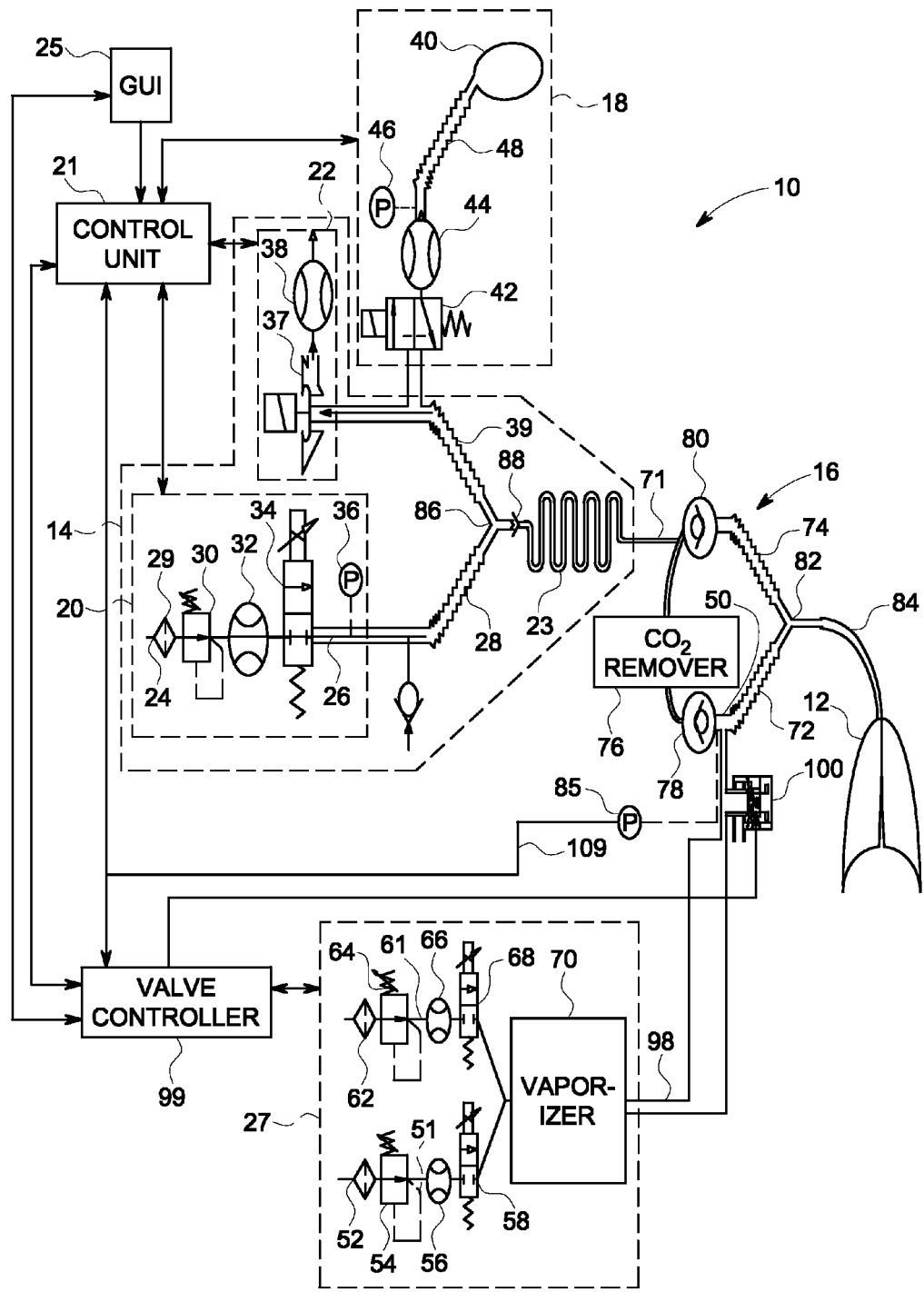
FIG. 1 illustrates an operational diagram for providing an inspiration gas for a subject breathing and for relieving a gaseous pressure of an inspiration limb in accordance with an embodiment of the present invention.

An arrangement 10 for providing an inspiration gas to a subject 12 utilizing a re-breathing circuit is shown in FIG. 1. It must be noted that FIG. 1 shows only a specific example of the arrangement 10 and it may vary depending on clinical needs. The arrangement of FIG. 1 comprises a machine ventilator circuit 14 for assisting breathing functions of the subject, a breathing circuit 16 for connecting lungs of the subject and the machine ventilator circuit 14 to exchange the gas in the lungs, a manual ventilation circuit 18 for enabling the manual ventilation of the subject and a control unit 21 for controlling an operation of the arrangement 10. The manual ventilation circuit 18 and the machine ventilator circuit 14 can be alternatively selected by an operator. The manual ventilation circuit can be in a gas flow connection with at least a part of the machine ventilator circuit for making a pneumatic contact with the lungs of the subject when the manual ventilation method is chosen. The arrangement 10 shown in FIG. 1 may also comprise a user interface 25 for entering any information needed while ventilating the subject and a gas mixer 27 for supplying a fresh gas for the subject breathing.

The machine ventilator circuit 14 generally comprises an inspiration delivery unit 20 for delivering the gas such as drive gas needed to enable an inspiration of the subject, an expiration circuit 22 for controlling a discharge of the expiration gas and a reciprocating unit 23 such as a well-known bellows and bottle combination, where the bellows are arranged within the bottle, or a long gas flow channel as shown in FIG. 1 for compressing the gas under a control of the drive gas pressure towards lungs of the subject to facilitate the inspiration. Both the inspiration delivery unit 20 and the expiration circuit 22 are controlled by the control unit 21.

As illustrated in FIG. 1, the inspiration delivery unit 20 comprises a compressed gas interface 24 connected to a compressed gas supply (not shown). The compressed gas can be either oxygen or air. Also a mechanism selecting the other if one gets de-pressurized can be applied (not shown). The inspiration delivery unit 20 comprises also a filter 29 for filtering impurities, a pressure regulator 30 for regulating a pressure of gases flowing from the gas interface, a flow sensor 32 for measuring an inspiration delivery flow from the gas interface and a flow control valve 34 for opening or closing the inspiration delivery flow. The flow sensor 32 and flow control valve 34 are each coupled to the control unit 21 to control the inspiration delivery to the subject 12. Further the inspiration delivery unit 20 may comprise a pressure sensor 36 for measuring the gas pressure flowing along the conduit 26 and an inspiration branch 28 towards the reciprocating unit 23.

The expiration circuit 22 comprises an expiration valve 37 for discharging the expiration gas and a flow sensor 38, which is optional, for measuring the flow discharged through the expiration valve 37. The expiration circuit is in flow connection along an expiration branch 39 with the reciprocating unit 23 and the manual ventilation circuit 18.

The manual ventilation circuit 18 comprises a manual bag 40 for providing a gas flow such as drive gas flow to increase a pressure needed for the subject inspiration and for receiving the gas flow for the expiration when the subject is expiring, a bag valve 42 for connecting and disconnecting the drive gas flow between the manual bag 40 and the expiration branch 39, a sensor 44 such as a flow sensor for detecting a flow direction inside the manual ventilation circuit 18 and a pressure sensor 46 for measuring a pressure of the manual ventilation circuit 18.

The gas mixer 27 is arranged to supply the fresh gas through a fresh gas outlet 50 to the breathing circuit 16 for the subject breathing. Typically the fresh gas comprises of oxygen and air or nitrous oxide. Oxygen is delivered through an oxygen delivery line 51 comprising of a filter 52, a pressure regulator 54, an oxygen flow sensor 56 and an oxygen flow control valve 58. The air is delivered through an air delivery line 61 comprising of filter 62, a pressure regulator 64, an air flow sensor 66, and air flow control valve 68. For a delivery of nitrous oxide respective components may be provided (not shown). After metering the individual gas flows, they are merged together for fresh gas mixture delivered to a vaporizer 70 which completes the fresh gas mixture with a volatile anesthesia agent vapor before delivery to the breathing circuit 16 at the fresh gas outlet 50 and to the subject breathing.

The breathing circuit 16, which is operably connected to the machine ventilator circuit 14 at a breathing circuit connection 71 and to the fresh gas outlet 50, comprises an inspiration limb 72 for an inspired gas, an expiration limb 74 for an exhaled gas, a carbon dioxide ($CO_2$) remover 76 such as $CO_2$ absorber to remove or absorb carbon dioxide from the exhaled gas coming from the subject 12, a first one-way valve 78 for an inspired gas to allow an inspiration through the inspiration limb 72, a second one-way valve 80 for an expired gas to allow an expiration through the expiration limb 74, a branching unit 82 such as a Y-piece having at least three limbs, one of them being for the inspired gas, a second one being for the expired gas and a third one being for both the inspired and expired gases and being connectable to by means of a patient limb 84 to the lungs of the subject 12. The first one-way valve 78 allows only unidirectional gas flow through the inspiration limb 72 meaning that the gas flow direction is from the first one-way valve 78 towards the branching unit 82 and the lungs of the subject 12. Correspondingly the second one-way valve 80 allows only unidirectional gas flow through the expiration limb 74 in which case the gas flow direction is from the branching unit 82 towards the second one-way valve 80 and through this second one-way valve. Also the breathing circuit may comprise a pressure sensor 85 for measuring a pressure of the breathing circuit 16.

In mechanical ventilation the manual bag valve 42 is maintained closed. During the inspiration phase of the machine ventilation the expiration circuit 22 of the machine ventilator circuit 14 closes the expiration valve 37 under the control of the control unit 21. This guides the inspiration gas flow from the inspiration delivery unit 20 through the inspiration branch 28 of a gas branching connector 86 and through the connection 88 of the reciprocating unit 23 pushing the breathing gas out from the breathing circuit connection 71 to the breathing circuit 16. The inspiration gas delivery unit 20 controlled by the control unit 21 delivers the gas flow either to reach the given gas volume or a pressure at subject lungs. For this control the flow sensor 32 for measuring the inspiration flow and the pressure sensor 85 of the breathing circuit 16 are used. Also the volume delivered from the fresh gas mixer 27 is taken into consideration in the delivery of the gas volume.

The first one-way valve 78 for the inspired gas and the second one-way valve 80 for the expired gas of the breathing circuit 16 guide the gas flow direction in the circuit. The inspiration flow is guided through the carbon dioxide remover 76 to remove or absorb from the expiration gas carbon dioxide and further the carbon dioxide free gas is guided through the first one-way valve 78 for an inspired gas to the inspiration limb 72 where it is mixed with the fresh gas flow and therefrom through the branching unit 82 to the patient limb 84 and finally to the lungs of the subject 12.

At the end of the inspiration phase the breathing circuit 16 and the subject lungs are pressurized. For the expiration under the control of the control unit 21 the inspiration delivery flow control valve 34 is closed stopping the inspiration delivery and the expiration valve 37 is opened to allow the gas release from the expiration branch 39 of the drive gas branching connector 86 and further through the connection 88 from the reciprocating unit 23. This allows the pressure release and breathing gas flow from breathing circuit 16 and the lungs of the subject 12 to the reciprocating unit 23. The breathing gas flows from the subject 12 through the patient limb 84, the branching unit 82, the expiration limb 74, the second one-way valve 80 for the expired gas and the breathing circuit connection 71 to the reciprocating unit 23. The pressure release is controlled for a desired expiration pressure such as a positive end expiration pressure (PEEP) target, which may be set using the user interface 25. For this control the ventilator control 21 uses the breathing circuit pressure measured by the pressure sensor 85 and the expiration valve 37. The expiration gas flow may be measured using the flow sensor 38 located in this embodiment at the expiration branch 39 or at the outlet the expiration valve 37 as shown in FIG. 1.

For the manual ventilation the bag valve 42 is opened. Preferably, the bag valve 42 may be electrically or pneumatically actuated. However, that may also have a direct access actuator button or lever for immediate manual access as an alternative. The manual bag valve 42 provides a gas flow path from the expiration branch 39 of the machine ventilator circuit 14 through the sensor 44 for detecting the flow direction inside the manual ventilation circuit 18 and the bag branch 48 to the manual bag 40.

This sensor 44 is utilized to identify the bag operations including the flow to the manual bag 40 and out from the manual bag and to trigger the inspiration and expiration phases of the breath cycle when on the manual ventilation mode. Thus the sensor 44 produces for the control unit 21 a signal to determine the flow direction to guide the expiration circuit 22. As a response to the inspiration triggering, the expiration valve 37 of the expiration circuit 22 is closed to guide the bag compression-induced drive gas flow towards the lungs of the subject.

Whenever subject lungs are being connected to the breathing circuit 16 and receives gases from some pressure source such as from the machine ventilator circuit 20, the manual ventilation circuit 18 or even only from the gas mixer 27, a risk for a high airway pressure exists. This may cause damage to the subject and therefore the branching unit 82 including any breathing channel in flow communication with this branching unit providing inspiration gas for the subject breathing must have redundant means to relieve the pressure even in any single failure in the ventilation system. For this purpose the breathing circuit is equipped with a valve 100 for relieving gaseous pressure in the branching unit 82, which is in flow communication with the lungs of the subject. The valve 100 may be part of the arrangement 10 comprising the gas mixer 27 and possibly also part of one of the machine ventilator circuit 14 and the manual ventilation circuit 18 or both of them. The valve may be connected to the branching unit 82 or the inspiration limb 72 being in the flow communication with the branching unit in order to be able to relieve the pressure from the lungs of the subject 12 in case the overpressure may have been created. The valve 100 should advantageously be between the first one-way valve 78 and the patient limb 84 exchanging the breathing gas between the lungs and the breathing circuit 16. In this case the valve 100 is also in flow communication with the inspiration limb 72, which inspiration limb and the branching unit is as well between the first one-way valve 78 and the patient limb 84. An advantageous positioning of the valve 100 is in immediate communication with the fresh gas outlet 50 which outlet and a fresh gas tube 98 guiding the fresh gas from the gas mixer 27 through this fresh gas outlet 50 for the subject breathing is considered to be between the first one-way valve 78 and the patient limb 84. In case the valve 100 is in the fresh gas tube 98, it should advantageously be closer to the outlet 50 than to the gas mixer 27. With such positioning the pressure can still be relieved even in failure situations like expiration limb 74 occlusion or failure to open expiration valve 37 because of expiration circuit 22 or the control unit 21 failure.

The valve 100 allows intelligent breathing circuit pressure relief under an active control. For this purpose, the valve 100 is operationally connected to a valve controller 99 that is independent to the control unit 21 operating the expiration valve 37. Thus the expiration valve 37 may be under control of the control unit 21 and the valve 100 may be under the control of the valve controller 99. The valve controller 99 may have other tasks like controlling the gas mixer 27 and/or vaporizer 70 as shown in FIG. 1, or that may be dedicated only for the pressure relief function. In active operation the valve controller 99 acquires information of the breathing circuit pressure. This pressure is available through the pressure sensor 85. It is advantageous that both the valve controller 99 and the control unit 21 can acquire from the pressure sensor 85 the pressure signal. If the measured pressure exceeds a user given allowed branching unit breathing gas pressure limit information, then the valve controller 99 releases the pressure by submitting an opening command to the valve 100. For additional safety, the active closure may be limited to a force corresponding with 10-12 kPa pressure. Also it is possible to relieve the pressure of the branching unit 82 and thus the pressure of the lungs to ambient pressure if this is desired for some reason. A special overpressure hazard occurs if the expiration limb 74 or the expiration valve 37 gets occluded: The subject may still get pressurized through the open inspiration limb 72 but the pressure cannot be relieved because of the expiration occlusion. In order to mitigate this risk, the valve 100 advantageously communicates with the patient limb 84 through the branching unit 82 and the inspiration limb 72 through which the lungs of the subject 12 are also pressurized.

Figure 2:
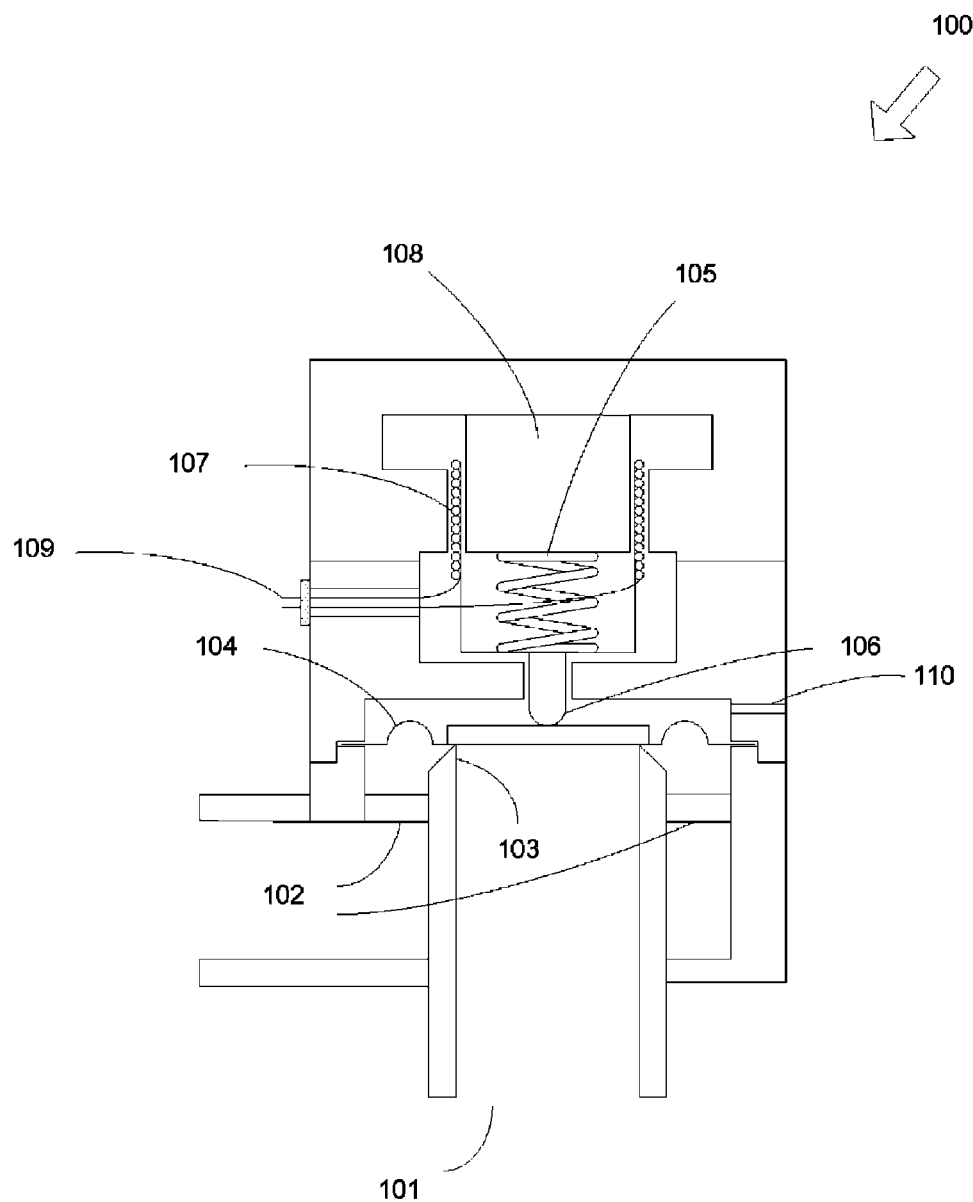
FIG. 2 is a cross sectional diagram of a valve t for relieving a gaseous pressure in accordance with an embodiment of the present invention.

Detailed description of the valve 100 is presented in FIG. 2. The valve has an inlet port 101 in flow communication with the branching unit 82 and outlet port 102 to discharge a gas flow from the inlet port to release the pressure through the inlet port 101. The outlet port may be connected to gas scavenging system or open to ambient as shown in FIG. 1. A valve seat 103, which is in flow communication with the inlet port 101, and a valve member 104 such as a valve membrane form the valve function. A closing spring 105 directing a predetermined closing force to the valve member 104 pushes the valve member 104 against the valve seat 103 using an optional stem 106. The stem is not necessarily needed in case the closing spring 105 has been arranged to push directly the valve member 104. The valve is able to close a gas discharge by means of the predetermined closing force when a pressure of the branching unit is below a pressure determined by the predetermined closing force and to facilitate the gas discharge when the pressure of the branching unit is above the pressure determined by the predetermined closing force. The valve member 104 can thus be pressed against the valve seat 103 to close the gas discharge between the inlet port 101 and the outlet port 102 and which member can be detached from the valve seat to facilitate the gas discharge between the inlet port and the outlet port.

To facilitate active pressure relief function, the valve 100 also accommodates an electronic actuator 107 connected to the valve controller 99 along a wire 109, the actuator being able to increase and decrease the closing force to the valve member. Thus this electrically operated actuator may, depending on its actuation, either exert additional closing force to the valve member 104, or operate against the predetermined closing force the closing spring 105 exerts on the valve member 104. This increase and decrease advantageously occurs through increase and decrease of the closing force of the closing spring 105. The stem 106 may be physically connected to the valve member 104 forcing the valve opening by the activation of the actuator 107 or alternatively the opening activation of the actuator 107 just lifts off the stem 106 from the valve member 104 allowing any pressure at the inlet port 101 above the prevailing ambient pressure on the opposite side of the valve member 104 through an opening 110 to freely escape through the open valve seat 103 to the outlet port 102.

As explained hereinbefore the valve is operationally connected to the valve controller 99, in which case the actuator 107 of the valve is operationally connected to the valve controller 99 allowing the valve controller to guide an operation of the valve or especially an operation of the actuator 107. The valve controller receives a signal indicative of a prevailing pressure of the branching unit 82 from the pressure sensor 85 enabling the valve controller to compare this pressure signal with the allowed branching unit breathing gas pressure limit information, which may be an upper pressure limit information or which may be advantageously maximum pressure limit information. This allowed branching unit breathing gas pressure limit information may be entered through the user interface 25 or set in the factory. If the prevailing pressure exceeds the allowed branching unit breathing gas pressure limit information the actuator is instructed to decrease the closing force to the valve member to reduce the prevailing pressure equal or below the allowed branching unit breathing gas pressure limit information to meet the allowed branching unit breathing gas pressure limit information. Typically the breathing gas pressure is released by allowing the valve member 104 loosen such as lift from the valve seat 103. This reduction may also result in prevailing pressure reduction to ambient pressure to prevent subject lung distension and blood circulation restriction by a sustained lung pressure. However, using the valve controller 99, the pressure of the branching unit 82 can also be released to any pressure below the user given allowed branching unit breathing gas pressure limit information if regarded advantageous for any reason. If the branching unit breathing gas upper pressure limit exceeds the pressure that the closing force of the closing spring 105 exerts on the valve member 104, the actuator 107 is controlled to exert additional force to add on the closing force exerted to the valve member 104. This addition may be continuous or occurring only when the signal indicative of the prevailing pressure informs the prevailing pressure approaches the predetermined pressure the closing spring 105 withstands.

The actuator 107 may be so called voice coil, a moving coil within a permanent magnet system comprised by a permanent magnet 108. Such device is ready for the required bi-directional actuation. Alternatively solenoid systems, where the stem 106 made of a magnetic material moves inside a coil the actuation of which creates a magnetic field. By nature such solenoid system is able to provide only uni-directional actuation and either two separate coils or additional permanent magnets will be required to meet the actuator requirements.

In its passive operating mode the actuator 107 is inactive. The spring force to the valve member and the surface area of the inlet port side of the valve member determines the valve opening pressure. In this mode the valve releases the pressures in excess to this threshold and closes when the inlet port pressure decreases back to the threshold. This functionality allows manually aided ventilation using the manual ventilation circuit 18 even though the electrical supply or the valve controller 99 fails. A predetermined spring force of the closing spring 105 is set to close a gas discharge between the inlet port 101 and said outlet port 102 up to breathing gas pressure of 2-6 KPa, more specifically 2-5 kPa, even more specifically 3-5 kPa. That is high enough for the manual ventilation and still provides safety against the overpressure of any patient.

For failure mode where the valve controller 99 erroneously commands the valve 100 to open, the control unit 21 may have access to switch off the control from controller 99 to the valve 100. A deactivation of the active control of the valve 100 allows the ventilation with pressures below the predetermined passive pressure level, and still have pressure limitation to this in the form of the passive closing force of the closing spring 105.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for ventilating lungs of a subject comprising a gas mixer for supplying a fresh gas for a subject breathing and a breathing circuit for connecting lungs of the subject and the gas mixer, the breathing circuit configured to provide an inspiration gas comprising the fresh gas for the subject breathing, the breathing circuit comprising:
    a branching unit comprising a Y-piece having at least three limbs, a first of the limbs being an inspiration limb for an inspired gas, the first limb having a first one-way valve to allow the inspired gas through the inspiration limb, a second of the limbs being an expiration limb for an expired gas, the second limb having a second one-way valve to allow the expired gas through the expiration limb, a third limb being a patient limb for carrying both the inspired gas and the expired gas to and from the lungs of a patient; and
    a valve configured to relieve gaseous pressure in the branching unit, the valve being coupled to one of the Y-piece and the first limb and between the first one-way valve and the patient limb, the valve comprising:
        an inlet port in flow communication with the branching unit;
        an outlet port configured to release pressure by discharging a gas flow from the inlet port;
        a valve seat in flow communication with the inlet port;
        a valve member configured to close a gas discharge between the inlet port and the outlet port when forced against the valve seat, and to facilitate gas discharge between the inlet port and the outlet port when not forced against the valve seat;
        a closing spring configured to direct a predetermined closing force to the valve member, wherein the valve member is not forced against the valve seat when a force, due to the gaseous pressure exerted on the valve member when the gas flows from the inlet port to the outlet port, exceeds the predetermined closing force of the closing spring; and
        an actuator configured to increase and decrease the closing force directed to the valve member;
            a valve controller configured to control an operation of the actuator, the valve controller being independent of a control unit operating an expiration valve of the second limb of the branching unit; and
            the closing spring configured to maintain the valve in a closed position when the actuator is inactive allowing manual ventilation through the branching unit in the event of a failure of the valve controller.

2. The system according to claim 1 further comprising:
    a machine ventilator circuit configured to assist breathing functions, wherein the machine ventilator circuit comprises an inspiration delivery unit configured to deliver a gas flow to assist an inspiration and an expiration circuit configured to control a discharge of an expiration gas; and
    a manual ventilation circuit configured to enable manual ventilation and assist breathing functions, the manual ventilation circuit comprising a manual bag to guide a gas from the manual bag.

3. A method for relieving gaseous pressure in a branching unit providing a breathing gas for a subject inhalation and receiving an exhaled breathing gas, the branching unit comprising a Y-piece having at least three limbs, a first of the limbs being an inspiration limb for an inspired gas, the first limb having a first one-way valve to allow the inspired gas through the inspiration limb, a second of the limbs being an expiration limb for an expired gas, the second limb having a second one-way valve to allow the expired gas through the expiration limb, a third limb being a patient limb for carrying both the inspired gas and the expired gas to and from the lungs of a patient, the branching unit being in flow communication with a valve comprising an inlet port and an outlet port, the valve configured to close a gas discharge with a predetermined closing force when a breathing gas pressure of the branching unit is below a pressure determined by the predetermined closing force and to facilitate the gas discharge when a force due to the breathing gas pressure of the branching unit exceeds the pressure determined by the predetermined closing force, the valve being coupled to one of the Y-piece and the first limb and between the first one-way valve and the patient limb, the method comprising:
    determining an allowed branching unit breathing gas pressure limit information;
    acquiring a signal indicative of a prevailing breathing gas pressure in the branching unit;
    changing the predetermined closing force if the allowed branching unit breathing gas pressure limit information deviates from the predetermined closing force;
    comparing the signal indicative of a prevailing breathing gas pressure with the allowed branching unit breathing gas pressure limit information;
    if the signal indicative of a prevailing breathing gas pressure deviates from the allowed branching unit breathing gas pressure limit information, changing the closing force to meet the allowed branching unit breathing gas pressure limit information;
    operating an actuator coupled to the valve for the step of changing the closing force;
    controlling the actuator independently from a control unit operating an expiration valve of the branching unit; and
    urging the valve in a closed position when the actuator is inactive and the breathing gas pressure is below the closing force, and allowing the valve to open when the gas pressure exceeds the closing force as the gas flows from the inlet port to the outlet port.

4. The method according to claim 3, wherein, if the signal indicative of a prevailing breathing gas pressure exceeds the allowed branching unit breathing gas pressure limit information, decreasing the closing force with the actuator that is electrically operated to meet the allowed branching unit breathing gas maximum pressure limit information.

5. The method according to claim 3, wherein the predetermined closing force is set to close the gas discharge up to a breathing gas pressure of about 2 kPa to about 6 kPa.

6. The method according to claim 3, wherein the allowed branching unit breathing gas pressure limit information is entered through a user interface or set in a factory.

* * * * *